(12) United States Patent  
Kern et al.

(10) Patent No.: US 9,138,574 B2  
(45) Date of Patent: Sep. 22, 2015

(54) ANCHOR DEPLOYMENT FOR IMPLANTABLE MEDICAL DEVICES

(71) Applicant: Medtronic, Inc., Minneapolis, MN (US)

(72) Inventors: Michael J. Kern, St. Louis Park, MN (US); Bruce A. Behymer, Grant, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/314,676

(22) Filed: Jun. 25, 2014

(65) Prior Publication Data

US 2015/0005857 A1 Jan. 1, 2015

Related U.S. Application Data

(60) Provisional application No. 61/839,410, filed on Jun. 26, 2013.

(51) Int. Cl.
| | |
|---|---|
| *A61N 1/00* | (2006.01) |
| *A61N 1/05* | (2006.01) |
| *A61M 25/02* | (2006.01) |

(52) U.S. Cl.
CPC .............. *A61N 1/05* (2013.01); *A61M 25/02* (2013.01); *A61M 2025/028* (2013.01); *A61M 2025/0286* (2013.01); *A61N 1/059* (2013.01); *A61N 1/0558* (2013.01); *A61N 2001/0582* (2013.01)

(58) Field of Classification Search
CPC .............. A61M 2025/028; A61M 2025/0286; A61M 25/02; A61N 1/05; A61N 1/0558; A61N 1/059; A61N 2001/0582
See application file for complete search history.

(56) References Cited

U.S. PATENT DOCUMENTS

| 5,824,032 | A | * | 10/1998 | Belden ........................ 607/126 |
| 6,999,819 | B2 | * | 2/2006 | Swoyer et al. .............. 607/117 |
| 2011/0040257 | A1 | | 2/2011 | Behymer et al. |
| 2012/0232624 | A1 | | 9/2012 | Sage |

FOREIGN PATENT DOCUMENTS

| WO | WO 2012/103123 | 8/2012 |
| WO | WO 2014/143485 | 9/2014 |

OTHER PUBLICATIONS

PCT/US2014/044096 Search Report and Written Opinion dated Jan. 27, 2015.

* cited by examiner

*Primary Examiner* — George Manuel

(57) ABSTRACT

A tool for deploying an anchor sleeve onto one or more implantable medical device bodies includes a holding element, on which the sleeve is mounted, and a base member having a channel, which receives the element in sliding engagement. A conduit of the holding element receives the one or more elongate bodies in sliding engagement. A deployment tip forms an opening of the channel, through which the holding element extends in sliding engagement, and which engages the mounted anchor sleeve for deployment thereof. The deployment tip may be provided as a separate component, wherein a distal segment of the base member is configured for attachment therewith; as such, the tip may be part of a deployment assembly that also includes the holding element. The deployment assembly may be selected from a plurality thereof included in a kit along with the base member.

26 Claims, 10 Drawing Sheets

ANCHOR DEPLOYMENT FOR IMPLANTABLE MEDICAL DEVICES

TECHNICAL FIELD

The present disclosure pertains to implantable medical devices, and more particularly to anchor deployment apparatus and methods.

BACKGROUND

A variety of elongate implantable medical devices, for example, drug delivery catheters and medical electrical leads, are known in the art, for example, to couple a therapy delivery generator and/or diagnostic devices to a target site within a body of a patient, for example, in the spinal column or in any of a number of internal organs. Those skilled in the art are familiar with apparatus and methods for anchoring these implanted devices. FIG. 1A is a schematic depicting a surgical incision site 12 through which an exemplary medical device 110 has been implanted. FIG. 1A illustrates an elongate body of device 110, extending proximally out from site 12, and an anchor sleeve 15 surrounding the body, for example, with a relatively tight, interference fit, to facilitate anchoring of device 110 to subcutaneous fascia 14, for example, via sutures tied thereabout and sewn into the fascia 14. In order to properly position such a snug fitting anchor sleeve 10 around the body of implanted device 110, an anchor deployment tool may be employed. Examples of such a tool are described in a co-pending and commonly assigned United States patent application having the pre-grant publication no. 2011/0040257, and the Ser. No. 12/896,147. Yet, there is still a need for alternative anchor deployment tools and associated methods.

BRIEF DESCRIPTION OF THE DRAWINGS

The following drawings are illustrative of particular embodiments of the present disclosure and therefore do not limit the scope. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the disclosure in any way. Rather, the following description provides practical examples, and, after reading the present disclosure, those skilled in the art will recognize that some of the examples may have suitable alternatives.

Figure 1A:
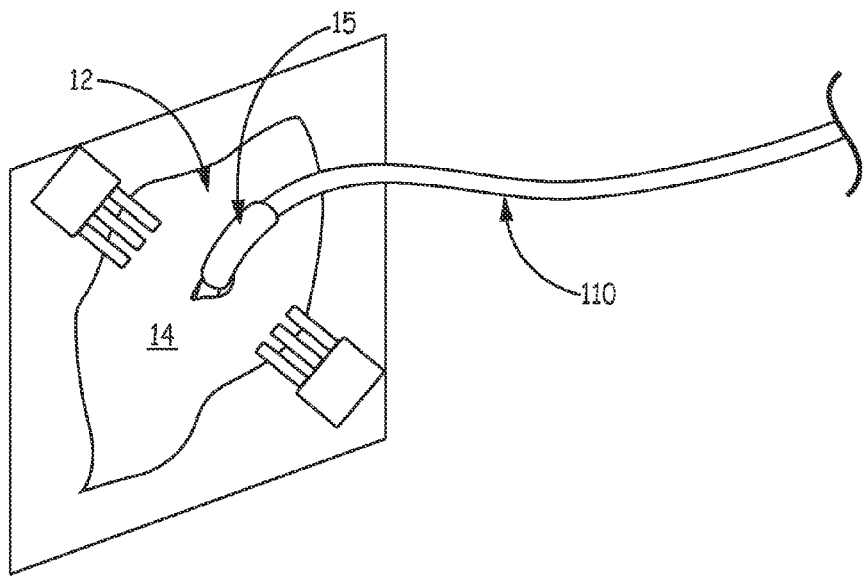
FIG. 1A is a schematic depicting a surgical incision site through which an exemplary medical device has been implanted.
Figure 1B:
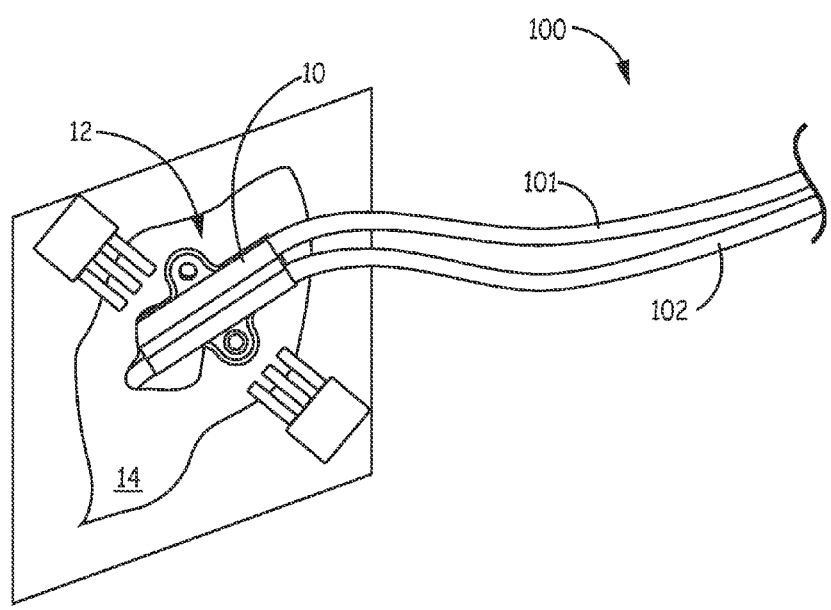
FIG. 1B is a schematic depicting the incision site through which an alternative exemplary medical device has been implanted.

FIG. 1B is a schematic depicting incision site 12 through which an exemplary medical device 100, which includes a pair of elongate bodies 101, 102, has been implanted. FIG. 1B illustrates each body 101, 102 being anchored together at site 12 by an anchor sleeve 10, which accommodates a side-by-side extension of bodies 101, 102 therethrough, for example, by a pair of lumens that extend side-by-side through sleeve 10, wherein each lumen receives one of bodies 101, 102. It should be noted that an alternate configuration of sleeve 10 may include a single lumen that is sized to accommodate bodies 101, 102 together therein. Medical device 100 may be a surgical medical electrical lead, in which one or more electrical conductors extend within each of bodies 101, 102 to an array of electrodes on a paddle-like assembly that terminates bodies 101, 102, at a distal end thereof. An example of such a lead is described in commonly assigned U.S. Pat. No. 7,738,966.

Figure 2A:
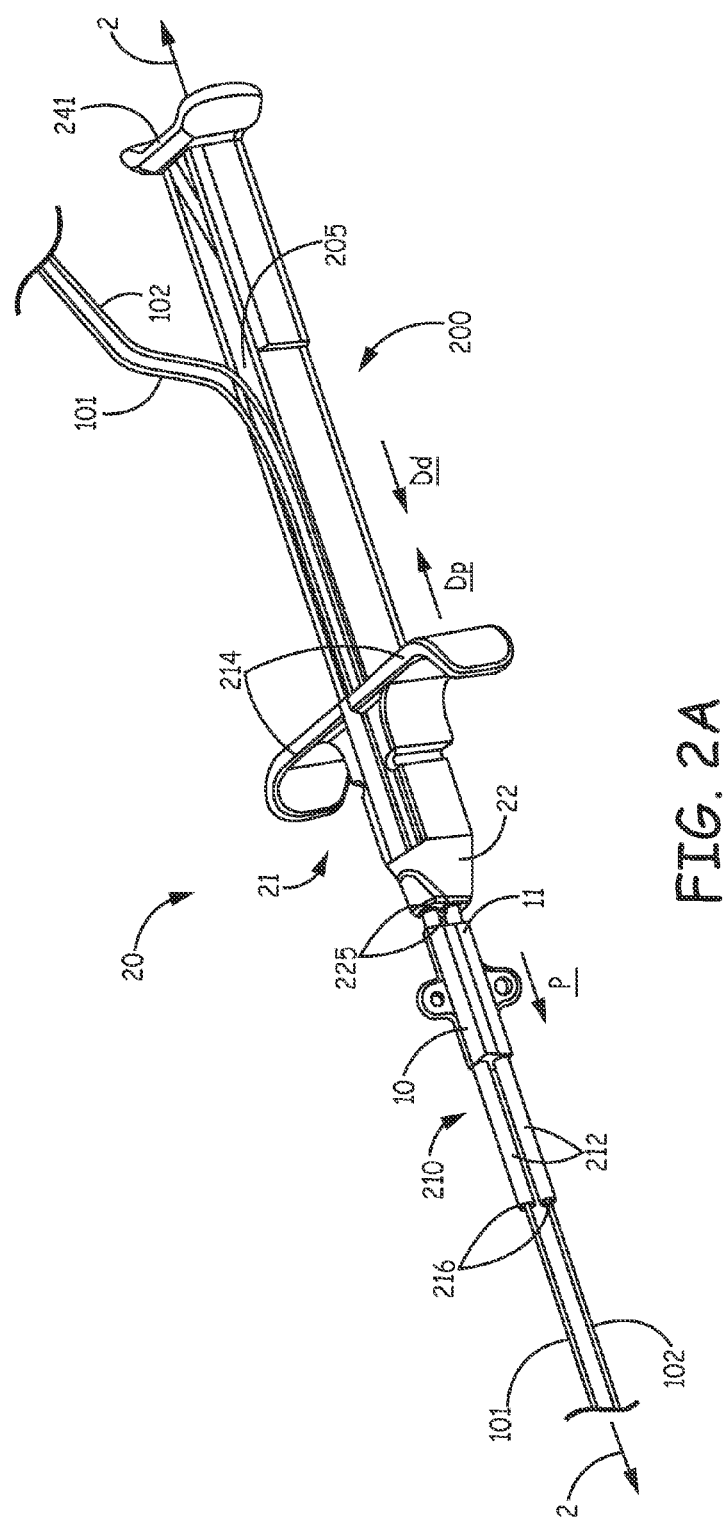
FIG. 2A is a perspective view of an exemplary anchor deployment tool positioned around a pair of elongate bodies of the exemplary medical device, and in a first position, according to some embodiments.
Figure 2B:
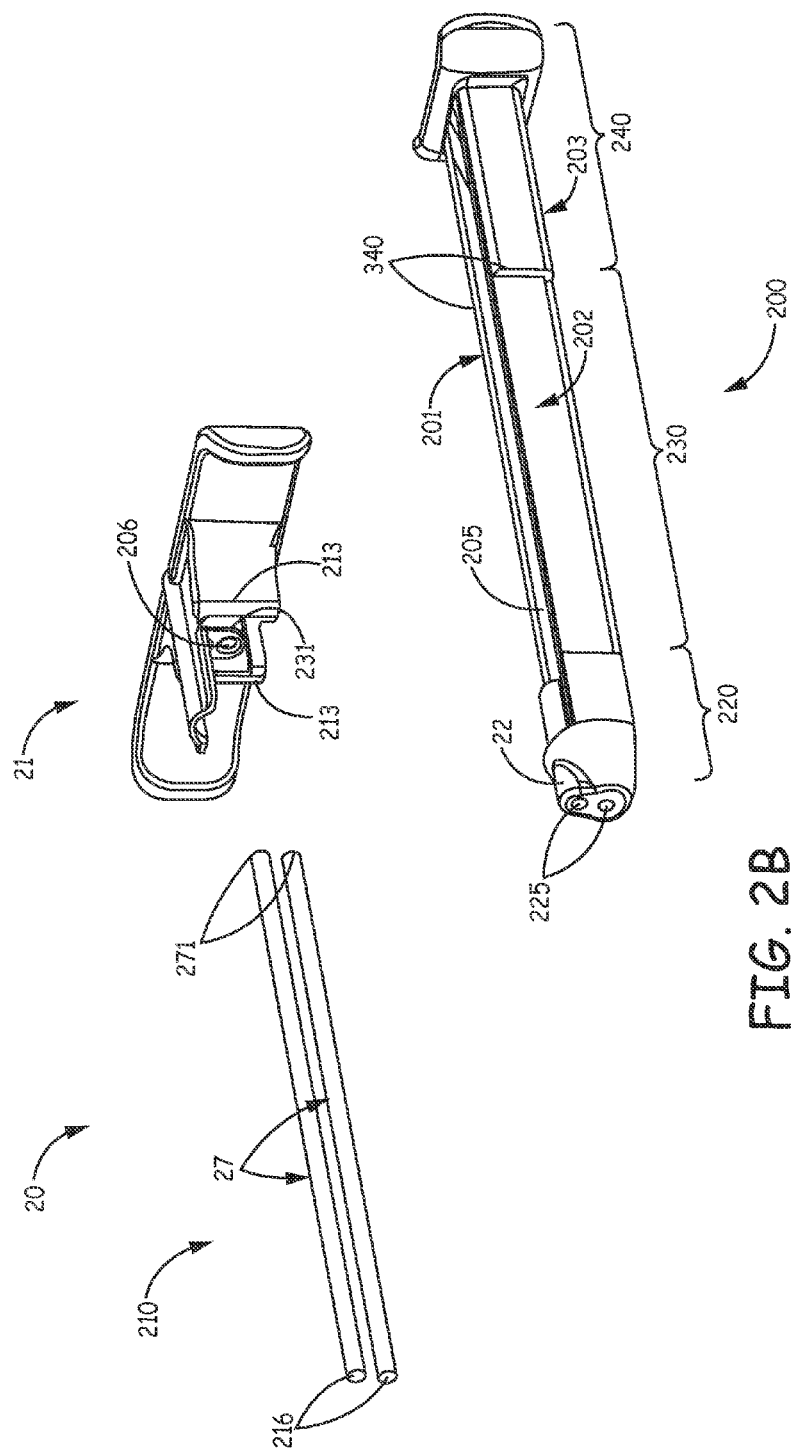
FIG. 2B is an exploded perspective view of the tool, according to some embodiments.

FIG. 2A is a perspective view of an exemplary anchor deployment tool 20, according to some embodiments, positioned around elongate bodies 101, 102 of the exemplary medical device 100 in order to deploy anchor sleeve 10 onto device 100 for subsequent anchoring thereof, for example, as shown in FIG. 1B. FIG. 2A illustrates tool 20 including a holding element 210 and a base member 200 that has a channel 205 to receive holding element 210 in sliding engagement therewith. Holding element 210 is shown having an outer surface 212 on which anchor sleeve 10 is mounted; and an inner surface of holding element defines a conduit 216 which receives lead bodies 101, 102 in sliding engagement. FIG. 2A further illustrates channel 205 of base member 200 defining a longitudinal axis 2 of tool 20, and extending proximally from an opening 225 thereof which is formed by a deployment tip 22 of base member 200. FIG. 2B is an exploded perspective view of tool 20, which provides a better view of opening 225. Opening 225 receives holding element 210 in sliding engagement, and holding element extends through opening 225 and into channel 205, so that conduit 216 is in communication with channel 205 to allow bodies 101, 102 to extend within channel 205, as shown in FIG. 2A.

Figure 2C:
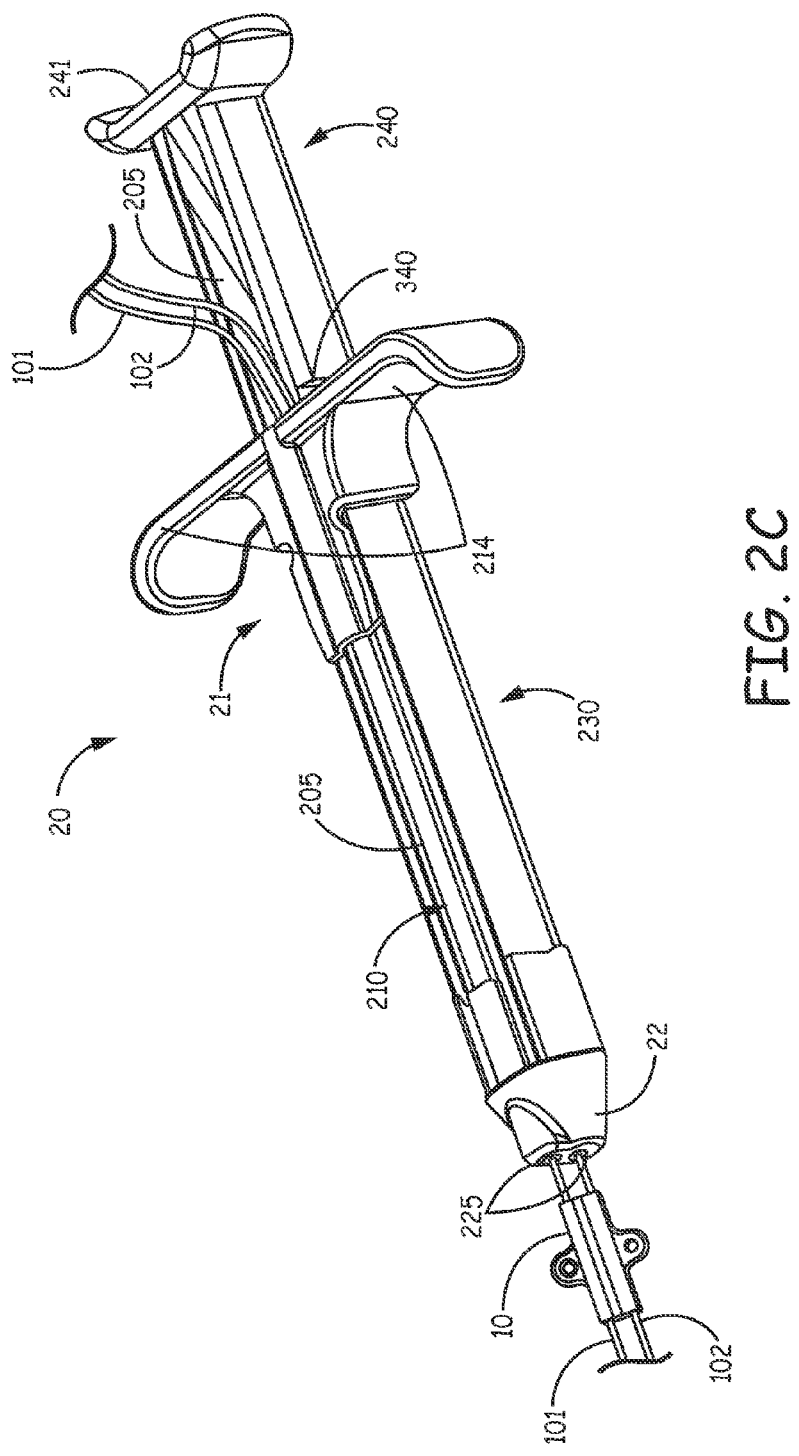
FIG. 2C is a perspective view of the tool in a second position, according to some embodiments.

According to the illustrated embodiment, holding element 210 has a handle member 21 attached to a proximal end 271 thereof (FIG. 2B), for example, to facilitate sliding holding element 210 and base member 200 relative to one another, for example, from a first position, which is illustrated in FIG. 2A, to a second position, which is illustrated in FIG. 2C (holding element 210, per arrow Dp, and base member 200, per arrow Dd). Laterally extending tab members 214 of handle member 21 can accommodate fingers of a hand of an operator, when a thumb of the operator is placed against an abutment surface 241 of base member 200. However, it should be noted that handle member 21 is an exemplary configuration for the proximal end of holding element 210, and does not necessarily limit the scope of the present disclosure.

Figure 4A:
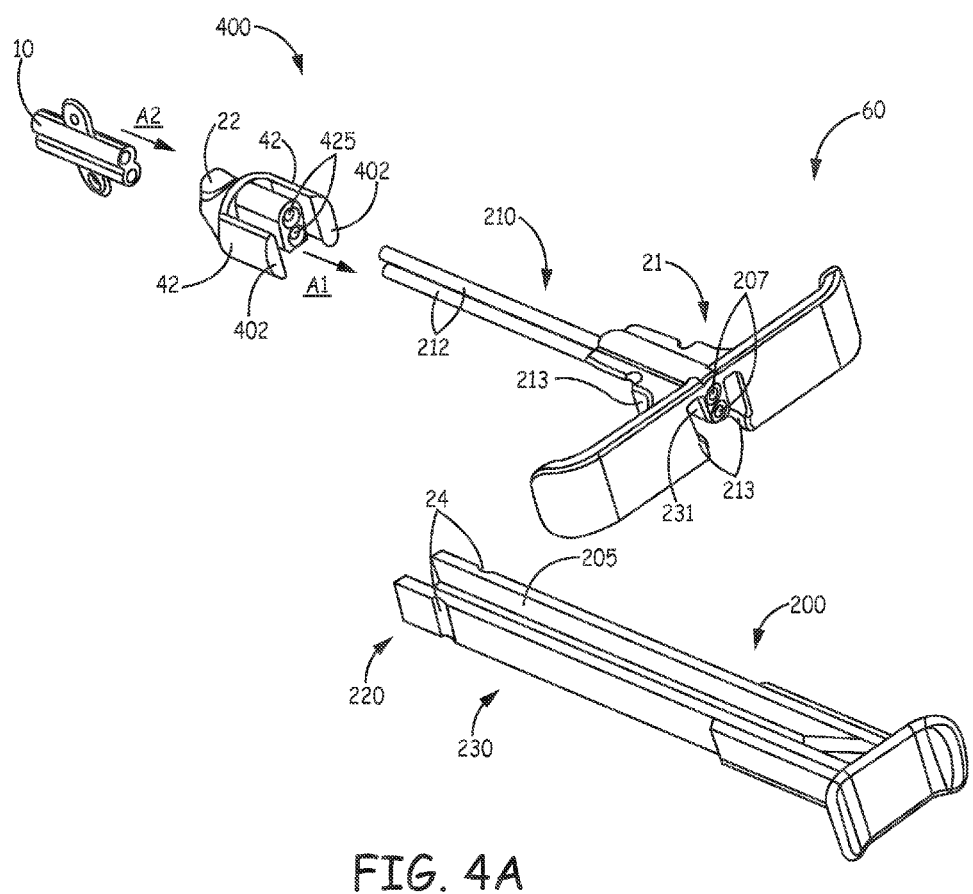
FIG. 4A is a perspective view of separate components, which are positioned relative to one another for assembly together into an exemplary anchor deployment tool, according to some methods and embodiments.

FIG. 2B illustrates holding element 210 including a pair of tubular members 27, wherein outer surface 212 of holding element 210 defines an outer diameter of each tubular member 27, and conduit 216 of holding element 210 is formed by a lumen of each member 27. However, in alternate embodiments, holding element 210 may be formed by a single member that has an inner and an outer surface sized to accommodate the pair of lead bodies 100, 102 and the aforementioned alternate configuration of sleeve 10, respectively. FIG. 2B further illustrates handle member 21 including an inner ridge 231, which is located between arms 213, and through which bores 206 are formed to receive proximal end 271 of each tubular member 27 for a press-fit attachment of holding element 210. With reference to FIG. 4A, a flared edge 207 of each proximal end 271 may abut a proximal surface of ridge 231 that surrounds a proximal opening of bores 206. According to some exemplary embodiments, base member 200 and handle member 21 are each formed, for example, by injection molding, from a suitable hard plastic material, for example, polycarbonate; and each tubular member 27 may be press fit into inner ridge 231 following molding, or handle member 21 may be insert molded around tubular members 27.

With reference back to FIG. 2A, deployment tip 22 of tool 20 is shown located in close proximity to an end 11 of the mounted anchor sleeve 10, and is configured to engage end 11, so that when holding element 210 and base member 200 are moved relative to one another, per arrows Dp, Dd, tip 22 pushes the mounted anchor sleeve 10, per arrow P, distally along outer surface 212 of holding element 210. Sleeve 10 is preferably formed from an elastic material, for example, medical grade silicone rubber, wherein each lumen of sleeve 10 has a relaxed inner diameter that is smaller than an outer diameter of each elongate body 101, 102 of device 100, so that sleeve 10 effectively grips around each body 101, 102, after being deployed thereon. Thus each lumen of sleeve 10 is stretched, or expanded, when mounted on outer surface 212. According to some embodiments, each tubular member 27 is a stainless steel hypo-tube with a lubricious coating forming outer surface 212, for example, a fluoropolymer coating (PTFE or ETFE), which can facilitate the assembly of sleeve 10 onto outer surface 212, as well as the movement of sleeve 10 therealong. FIG. 2C shows that, once holding element 210 and base member 200 reach the second position, sleeve 10 is deployed onto bodies 101, 102, and a length of holding element 210, on which sleeve 10 was mounted, at the first position, and during movement to the second position, is recessed proximally from opening 225 and contained within channel 205. Since conduit 216 of holding element 210, and channel 205 of base member 200 both receive bodies 101, 102 in sliding engagement, bodies 101, 102 can be held steady while sleeve 10 is deployed.

With further reference to FIG. 2B, base member 200 is shown including sidewalls 201, 202, and 203 that extend along a length of channel 205; sidewalls 201, 202, 203 are divided into a distal segment 220, a rail segment 230, and a proximal segment 240. Rail segment 230 is shown extending between distal segment 220, which is terminated by deployment tip 22, and shoulders 340 of proximal segment 240. According to the illustrated embodiment, handle member 21 includes a fitting feature formed by opposing arms 213 that engage with base member 200, along rail segment 230, for example, by wrapping around sidewalls 201, 202, to hold handle member 21 and the attached holding element 210 in sliding engagement with base member 200. With reference to FIG. 2C, it may be appreciated that shoulders 340 of proximal segment 240 provide a stop for the sliding engagement of handle member 21, which can prevent handle member 21 from pinching bodies 101, 102 within channel 205, during the deployment of sleeve 10.

Figure 3:
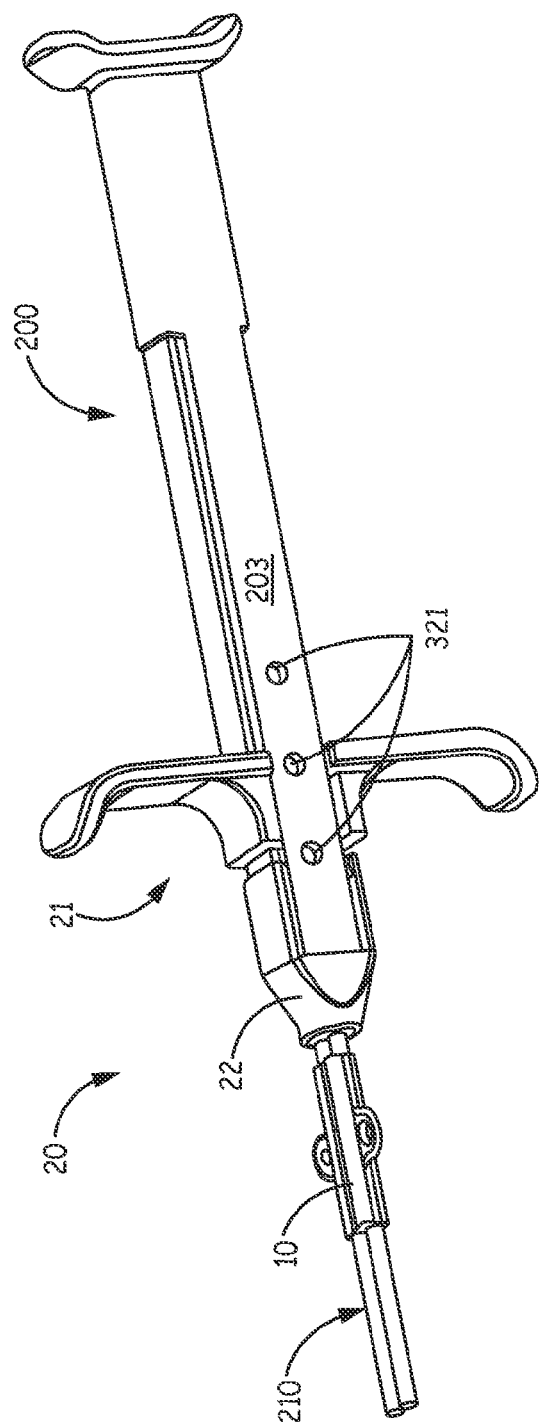
FIG. 3 is another perspective view of the tool, according to some embodiments.

FIG. 3 is another perspective view of tool 20 in which sidewall 203 may be seen. According to the illustrated embodiment, sidewall 203 is perforated, that is, includes holes 321 formed therethrough, along rail segment 230. Thus, if tool 20 is assembled for packaging, as shown in FIG. 3, sterilization gases may flow through holes 321 and into that portion of channel 205 where ridge 231 of handle member 21 is received.

Figure 4B:
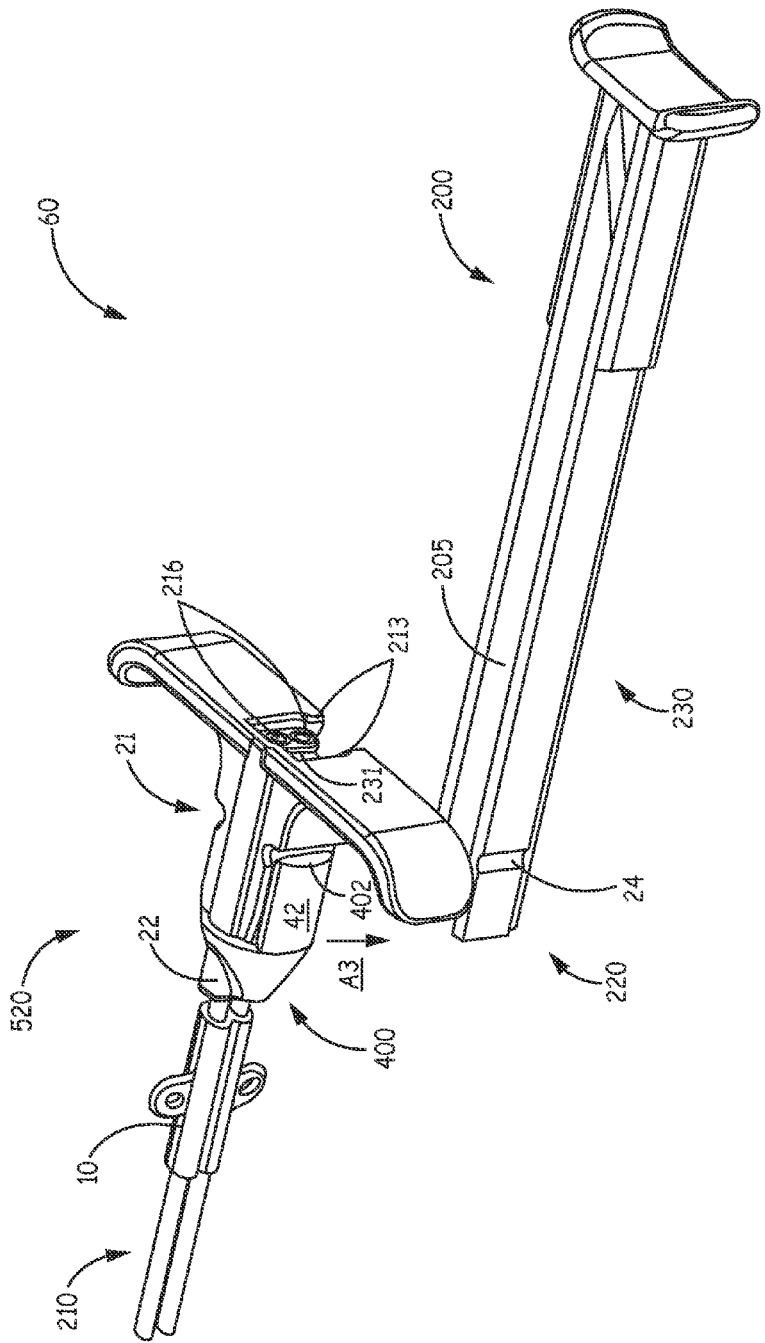
FIG. 4B is a perspective view of a deployment assembly formed from some of the components.

FIG. 4A is a perspective view of separate components, which are positioned relative to one another for assembly together into an exemplary anchor deployment tool 60, according to some methods and embodiments; and FIG. 4B is a perspective view of a deployment assembly 520 formed from some of the components. FIG. 4A illustrates the components including base member 200, anchor sleeve 10, a deployment tip component 400, and holding element 210, to which handle member 21 is attached, for example, as described above; channels 425 of tip component 400 are shown oriented for assembly around outer surface 212 of holding element 210, per arrow A1. With reference back to FIGS. 2A-C, channels 425 extend from openings 225 in deployment tip 22, and loosely fit around holding element 210 for sliding engagement of element 210 therethrough. FIG. 4B further illustrates anchor sleeve 10 oriented for mounting onto outer surface 212 of holding element 210, per arrow A2, after tip component 400 is assembled thereabout, in order to form deployment assembly 520 of FIG. 4B. A tapered lead-in tip (not shown) may be temporarily coupled to a distal end holding element 210 to facilitate the assembly of sleeve 10 onto outer surface 212. It should be noted that, holding element 210 of assembly 520 may have an inner surface configured to receive more than two elongate bodies of one or more medical devices, and, according to such an alternate embodiment, outer surface 212 of holding element 210 receives an appropriately sized anchor sleeve, and deployment tip 22 is configured for the appropriate 'loose' fit around holding element 210. An exemplary deployment tool 70, which accommodates three elongate medical device bodies 101, 102, 103 is described below in conjunction with FIG. 6.

FIG. 4B illustrates deployment assembly 520 positioned and oriented for assembly, for example, by moving handle member 21, per arrow A3, and pressing opposing arms 213 of handle member 21 into engagement around rail segment 230 of base member 200 so that holding element 210 (i.e., the portion thereof that extends between handle member 21 and tip component 400) and inner ridge 231 are received by channel 205 in sliding engagement with base member 200. According to the illustrated embodiment, distal segment 220 of base member 200 is configured for engagement with a fitting feature of tip component 400, wherein the fitting feature includes opposing arms 42, which extend proximally from deployment tip 22, and which have ends 402 to mate within grooves 24 formed in distal segment 220. (Arms 42 and ends 402 thereof are best seen in FIG. 4A.) FIG. 4B further illustrates ends 402 of opposing arms 42 approximately aligned with grooves 24, so that, when assembly 520 is moved, per arrow A3 to press handle member 21 into engagement with base member 200, ends 402 of arms 42 slide into grooves 24, and, once mated therewith, hold tip component 400 in fixed relation with base member 200 while holding element 210 and base member 200 are free to slide relative to one another, for example, between the above described first and second positions.

Figure 5:
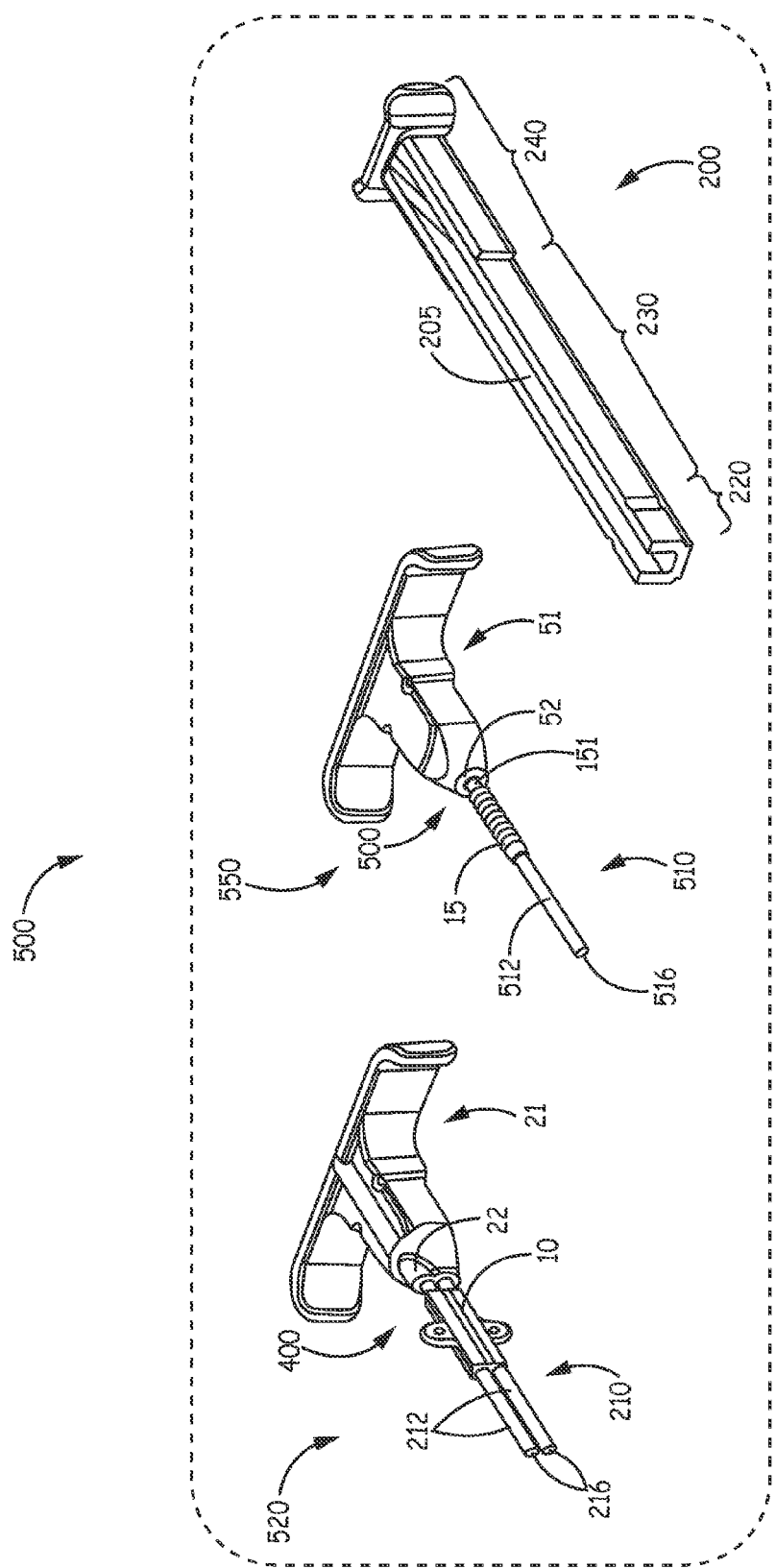
FIG. 5 is a perspective view of an exemplary tool kit, according to some embodiments.

FIG. 5 is a perspective view of an exemplary tool kit 500, according to some embodiments, from which various tools may be formed for deploying an anchor sleeve onto a medical device. FIG. 5 illustrates kit 500 including base member 200, deployment assembly 520, and an alternate deployment assembly 550, to accommodate an operator who is implanting a medical device like device 110 (FIG. 1A), or an operator who is implanting a medical device like device 100 (FIG. 1B). Thus, according to some methods of the present disclosure, an operator who has implanted device 100, may select, and remove from kit 500, deployment assembly 520, along with base member 200, to form a deployment tool, for example, like tool 60 described above, either before or after inserting proximal lengths of elongate bodies 101, 102 through conduit 216. The tool may be formed according the method described above, in conjunction with FIG. 4B, and then sleeve 10 may be deployed by moving base member 200 and holding element 210 relative to one another from the first position of FIG. 2A to the second position of FIG. 2C, as is also described above. As mentioned above, assembly 520 may be configured to accommodate more than two elongate bodies of one or more medical devices, or kit 500 may include another deployment assembly thus configured, according to some alternate embodiments.

With reference back to FIG. 1A, an operator who has implanted device 110 may select deployment assembly 550 from kit 500, for assembly with base member 200, to form a tool to deploy anchor sleeve 15 onto the single body of device 110. Deployment assembly 550 is shown including a holding element 510 having an outer surface 512 on which sleeve 15 mounted and an inner surface defining a conduit 516 to receive body of device 110 in sliding engagement. FIG. 5 further illustrates holding element 510 having a handle member 51 attached to a proximal end thereof, for example, in a similar fashion to that described above for handle member 21 and holding element 210. Furthermore, a tip component 500 of assembly 550 is configured for assembly together with base member 200 in the manner described above for tip component 400 of assembly 520, and, once assembled together, a deployment tip 52 of component 500 may engage with an end 151 of sleeve 15 to push sleeve off of outer surface 512 of holding element 510 and onto body of device 110, which is received within conduit 516 (not shown).

Figure 6:
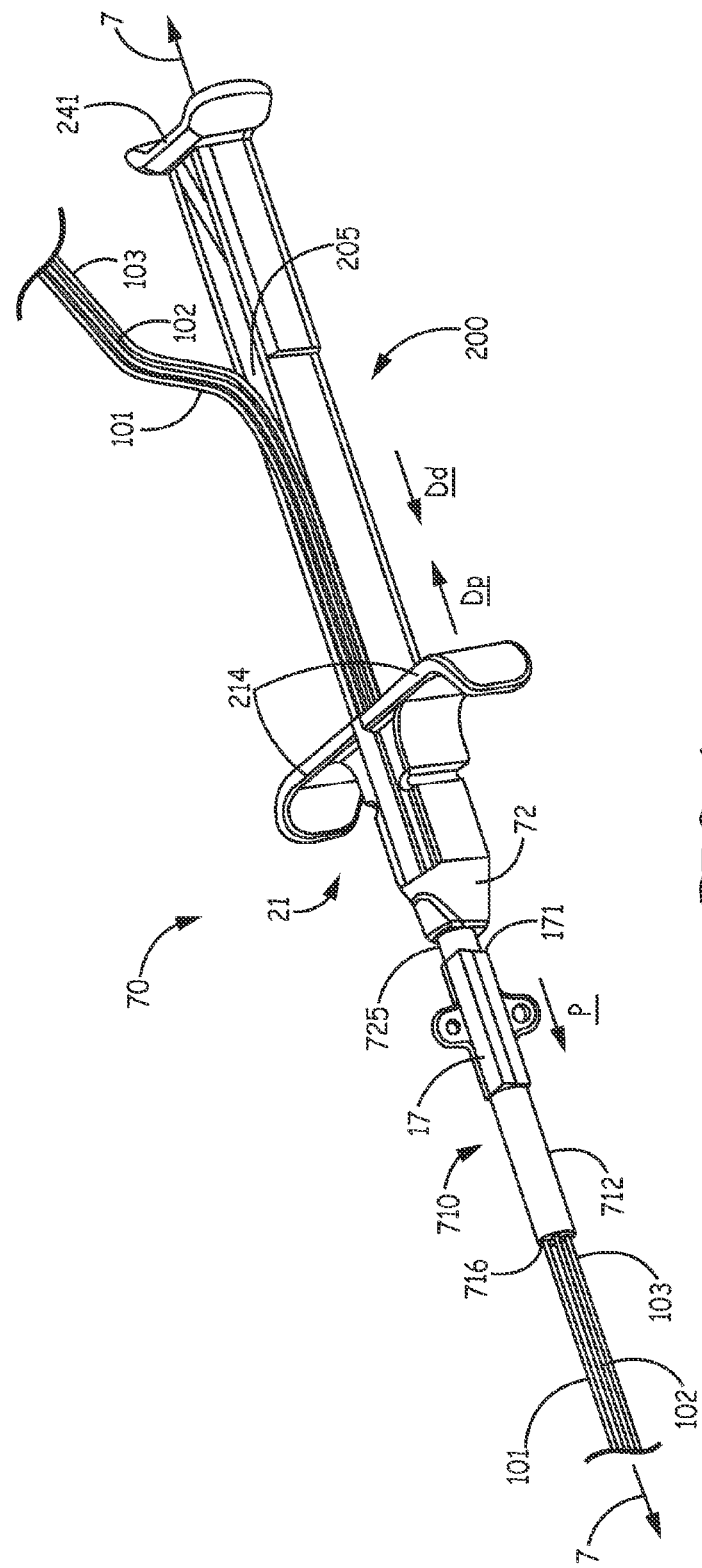
FIG. 6 is a perspective view of an exemplary anchor deployment tool positioned around a plurality of elongate medical device bodies, according to some alternate embodiments.

FIG. 6 is a perspective view of the aforementioned exemplary anchor deployment tool 70 positioned around a plurality of elongate medical device bodies 101, 102, 103, according to some alternate embodiments. Bodies 101, 102, 103 may all be portions of a single implantable medical device or make up more than one implantable medical device. FIG. 6 illustrates an anchor sleeve 17 mounted on an outer surface 712 of a holding element 710 of tool 70 and bodies 101, 102, 103 extending, in sliding engagement, within a conduit 716 formed by an inner surface of holding element 710. Like tool 20, described above, tool 70 includes base member 200 that has a channel 205; channel 205 defines a longitudinal axis 7 of tool 70 and extends from an opening 725 thereof, which is formed by a deployment tip 72 of base member 200. According to the illustrated embodiment, holding element 710 extends through opening 725 and into channel 205, to be received in sliding engagement with base member 200, in a similar fashion to that described above for holding member 210 of tool 20. Thus, conduit 716 is in communication with channel 205 to allow elongate medical device bodies 101, 102, 103 to extend within channel 205. In some embodiments, deployment tip 72 is part of a separate tip component, similar to component 400 described above.

With further reference to FIG. 6, holding element 710 has handle member 21 attached thereto, for example, to facilitate sliding holding element 710 and base member 200 relative to one another, for example, as described above for tool 20 (holding element 710, per arrow Dp, and base member 200, per arrow Dd). Deployment tip 72 is shown located in close proximity to an end 171 of the mounted anchor sleeve 17, and is configured to engage end 171, so that when holding element 710 and base member 200 are moved relative to one another, per arrows Dp, Dd, tip 72 pushes the mounted anchor sleeve 17, per arrow P, distally along outer surface 712 of holding element 710. Sleeve 17 may be formed from an elastic material, for example, medical grade silicone rubber, which is stretched, or expanded, for mounting on outer surface 712, and has a relaxed inner diameter that is smaller than an outer diameter of elongate bodies 101, 102, 103, so that sleeve 17 can effectively grip around each body 101, 102, 103 after being deployed thereon. According to some embodiments, holding element 710 is formed by one or more stainless steel hypo-tubes with a lubricious coating forming outer surface 712, for example, a fluoropolymer coating (PTFE or ETFE), which can facilitate the assembly of sleeve 17 onto outer surface 712, as well as the movement of sleeve 17 therealong when being deployed by tip 72. Since conduit 716 of holding element 710, and channel 205 of base member 200 both receive bodies 101, 102, 103 in sliding engagement, bodies 101, 102, 103 can be held steady while sleeve 17 is deployed.

In the foregoing detailed description, specific exemplary embodiments have been described. However, it may be appreciated that various modifications and changes can be made without departing from the scope of the disclosure as set forth in the appended claims. Furthermore, deployment tools and kits for forming deployment tools, which include various combinations of features described above in conjunction with the specific embodiments, are within the scope of the present invention, for example, according to the following 15 statements that disclose features or combinations of features in exemplary embodiments:

1. In some exemplary embodiments, a tool for deploying an anchor sleeve onto at least one implantable medical device, the tool comprising: a holding element comprising an outer surface and an inner surface, the outer surface being configured to receive an anchor sleeve mounted thereon, and the inner surface defining a conduit of the holding element, the conduit being configured to receive, in sliding engagement, a plurality of elongate implantable medical device bodies; and a base member comprising a deployment tip and a channel, the channel defining a longitudinal axis of the tool and extending proximally from an opening thereof, the deployment tip forming the opening of the channel, the channel receiving the holding member in sliding engagement with the base member, and the conduit of the holding element being in communication with the channel; wherein the holding element and the base member slide relative to one another between a first position and a second position, the first position at which the holding element extends through the opening of the channel and distally from the deployment tip of the base member, over a length sufficient to receive the mounting of the anchor sleeve on the outer surface thereof, and the second position at which the length of the holding element is recessed proximally from the opening; and the deployment tip of the base member is configured to engage an end of the anchor sleeve, when the anchor sleeve is mounted on the holding element, the engagement with the end of the anchor sleeve for pushing the mounted anchor sleeve distally along the outer surface of the holding element as the holding element and base member slide from the first position to the second position.

2. The exemplary embodiment according to statement 1, further comprising a handle member attached to a proximal end of the holding element, the handle member configured to facilitate sliding the base member and the holding element relative to one another.

3. The exemplary embodiment according to statement 2, wherein the handle member includes opposing arms and an inner ridge located therebetween, the proximal end of the holding element being attached to the inner ridge of the handle member, and the opposing arms engage the base member so that the inner ridge is located within the channel of the base member.

4. The exemplary embodiment according to statement 2, further comprising: a handle member attached to a proximal end of the holding element, the handle member including opposing arms engaging the base member, and the handle member being configured to facilitate sliding the base member and the holding element relative to one another; and wherein the base member includes a distal segment, a rail segment, and a proximal segment, the distal segment being terminated by the deployment tip, the rail segment extending between the distal segment and shoulders of the proximal segment, and the channel extending through the distal segment, and through the rail segment, and into the proximal segment; and the opposing arms of the handle member engage around the rail segment of the base member to hold the handle member and the attached holding element in sliding engagement with the base member, along the rail segment thereof, the sliding engagement being stopped by the shoulders of the proximal segment.

5. The exemplary embodiment according to any of statements 1-4, wherein the deployment tip of the base member is a separate component attached to the base member; and the base member further comprises a sidewall extending along a length of the channel, the sidewall including a distal segment configured for the attachment of the deployment tip.

6. The exemplary embodiment according to any of statements 1-5, wherein the holding element comprises two or more tubular members extending side-by-side and approximately parallel with one another, the outer surface of the holding element defining an outer diameter of each tubular member, the conduit of the holding element comprising a lumen of each of the tubular members, and the proximal end of the holding element comprising a proximal end of each tubular member.

7. The exemplary embodiment according to any of statements 1-6, wherein the base member further comprises a perforated sidewall extending along a length of the channel.

8. The exemplary embodiment according to any of statements 1-7, wherein the outer surface of the holding member comprises a lubricious coating.

9. In some alternative exemplary embodiments, a tool for deploying an anchor sleeve onto at least one implantable medical device, the tool comprising: a holding element comprising an outer surface and an inner surface, the outer surface being configured to receive an anchor sleeve mounted thereon, and the inner surface defining a conduit of the holding element, the conduit configured to receive, in sliding engagement, at least one elongate body of the at least one implantable medical device; a deployment tip comprising at least one opening configured to receive the holding element extending therethrough in sliding engagement; and a base member comprising a channel and a sidewall, within which the channel extends, the sidewall including a distal segment configured for attachment of the deployment tip thereto; wherein, when the deployment tip is attached to the distal segment of the base member, and the holding element extends through the at least one opening of the deployment tip, the channel of the base member receives the holding element in sliding engagement therewith, so that the conduit of the holding element is in communication with the channel, and the holding element and the base member slide relative to one another between a first position and a second position, the first position at which the holding element extends distally from the attached deployment tip, and over a length sufficient to receive the mounting of the anchor sleeve on the outer surface thereof, and the second position at which the length of the holding element is recessed proximally from the at least one opening of the attached deployment tip; and the deployment tip is configured to engage an end of the anchor sleeve, when the anchor sleeve is mounted on the holding element, the deployment tip is attached to the base member, and the holding element extends through the at least one opening of the deployment tip, the engagement with the end of the anchor sleeve for pushing the mounted anchor sleeve distally along the outer surface of the holding element as the holding element and base member slide from the first position to the second position.

10. The exemplary embodiment according to statement 9, wherein the deployment tip further comprises opposing arms; and the distal segment of the sidewall of the base member includes grooves configured to mate with ends of the opposing arms of the deployment tip, for the attachment of the deployment tip to the distal segment.

11. The exemplary embodiment according to statement 9 or 10, further comprising: a handle member attached to a proximal end of the holding element, the handle member configured to facilitate sliding the base member and the holding element relative to one another, when the holding element extends through the at least one opening of the attached deployment tip; and wherein the handle member includes opposing arms and an inner ridge, the proximal end of the holding element being attached to the inner ridge of the handle member; and the opposing arms engage the base member so that the inner ridge is located within the channel of the base member.

12. The exemplary embodiment according to statement 9 or 10, further comprising: a handle member attached to a proximal end of the holding element, the handle member configured to facilitate sliding the base member and the holding element relative to one another, when the holding element extends through the at least one opening of the attached deployment tip; and wherein the sidewall of the base member further includes a rail segment and a proximal segment, the rail segment extending between the distal segment and shoulders of the proximal segment; and the handle member includes opposing arms that engage the rail segment of the sidewall of the base member, to hold the handle member and attached holding element in sliding engagement with the base member, along the rail segment, the sliding engagement being stopped by the shoulders of the proximal segment.

13. The exemplary embodiment according to any of statements 9-12, wherein the holding element comprises two or more tubular members extending side-by-side and approximately parallel with one another, the outer surface of the holding element defining an outer diameter of each tubular member, and the conduit of the holding element comprising a lumen of each of the tubular members.

14. The exemplary embodiment according to any of statements 9-13, wherein the outer surface of the holding member comprises a lubricious coating.

15. An exemplary embodiment of a tool kit for forming a tool according to any of statements 9-14, wherein the tool kit includes a base member according to any of statements 9-14, and a plurality of deployment assemblies from which to select for attachment to the base member, at least one of the plurality of deployment assemblies including a holding element and a deployment tip according to any of statements 9-14.

We claim:

1. A tool for deploying an anchor sleeve onto at least one implantable medical device, the tool comprising:
   a holding element comprising an outer surface and an inner surface, the outer surface being configured to receive an anchor sleeve mounted thereon, and the inner surface defining a conduit of the holding element, the conduit being configured to receive, in sliding engagement, a plurality of elongate bodies of the at least one implantable medical device; and
   a base member comprising a deployment tip and a channel, the channel defining a longitudinal axis of the tool and extending proximally from an opening thereof, the deployment tip forming the opening of the channel, the channel receiving the holding element in sliding engagement with the base member, and the conduit of the holding element being in communication with the channel;
   wherein the holding element and the base member slide relative to one another between a first position and a second position, the first position at which the holding element extends through the opening of the channel and distally from the deployment tip of the base member, over a length sufficient to receive the mounting of the anchor sleeve on the outer surface thereof, and the second position at which the length of the holding element is recessed proximally from the opening; and
   the deployment tip of the base member is configured to engage an end of the anchor sleeve, when the anchor sleeve is mounted on the holding element, the engagement with the end of the anchor sleeve for pushing the mounted anchor sleeve distally along the outer surface of the holding element as the holding element and base member slide from the first position to the second position.

2. The tool of claim 1, wherein the holding element comprises at least two tubular members extending side-by-side and approximately parallel with one another, the outer surface of the holding element defining an outer diameter of each tubular member, and the conduit of the holding element comprising a lumen of each of the tubular members.

3. The tool of claim 1, further comprising a handle member attached to a proximal end of the holding element, the handle member configured to facilitate sliding the base member and the holding element relative to one another.

4. The tool of claim 3, wherein the handle member includes opposing arms and an inner ridge located therebetween, the proximal end of the holding element being attached to the inner ridge of the handle member, and the opposing arms engage the base member so that the inner ridge is located within the channel of the base member.

5. The tool of claim 4, wherein the holding element comprises at least two tubular members extending side-by-side and approximately parallel with one another, the outer surface of the holding element defining an outer diameter of each tubular member, the conduit of the holding element comprising a lumen of each of the tubular members, and the proximal end of the holding element comprising a proximal end of each of the tubular members.

6. The tool of claim 5, wherein the proximal end of each tubular member is press fit within a bore hole formed through the inner ridge of the handle member, and each proximal end includes a flared edge that abuts a surface of the inner ridge, the surface extending around an opening of the corresponding bore hole.

7. The tool of claim 1, wherein the deployment tip of the base member is a separate component attached to the base member; and the base member further comprises a sidewall extending along a length of the channel, the sidewall including a distal segment configured for the attachment of the deployment tip.

8. The tool of claim 1, further comprising:
   a handle member attached to a proximal end of the holding element, the handle member including opposing arms engaging the base member, and the handle member being configured to facilitate sliding the base member and the holding element relative to one another; and
   wherein the base member includes a distal segment, a rail segment, and a proximal segment, the distal segment being terminated by the deployment tip, the rail segment extending between the distal segment and shoulders of the proximal segment, and the channel extending through the distal segment, and through the rail segment, and into the proximal segment; and
   the opposing arms of the handle member engage around the rail segment of the base member to hold the handle member and the attached holding element in sliding engagement with the base member, along the rail segment thereof, the sliding engagement being stopped by the shoulders of the proximal segment.

9. The tool of claim 8, wherein the holding element comprises at least two tubular members extending side-by-side and approximately parallel with one another, the outer surface of the holding element defining an outer diameter of each tubular member, the conduit of the holding element comprising a lumen of each of the tubular members, and the proximal end of the holding element comprising a proximal end of each tubular member.

10. The tool of claim 1, wherein the base member further comprises a perforated sidewall extending along a length of the channel.

11. The tool of claim 1, wherein the outer surface of the holding member comprises a lubricious coating.

12. A tool for deploying an anchor sleeve onto at least one implantable medical device, the tool comprising:
   a holding element comprising an outer surface and an inner surface, the outer surface being configured to receive an anchor sleeve mounted thereon, and the inner surface defining a conduit of the holding element, the conduit configured to receive, in sliding engagement, at least one elongate body of the at least one implantable medical device;
   a deployment tip comprising at least one opening configured to receive the holding element extending therethrough in sliding engagement; and
   a base member comprising a channel and a sidewall, within which the channel extends, the sidewall including a distal segment configured for attachment of the deployment tip thereto;
   wherein, when the deployment tip is attached to the distal segment of the base member, and the holding element extends through the opening of the deployment tip, the channel of the base member receives the holding element in sliding engagement therewith, so that the conduit of the holding element is in communication with the channel, and the holding element and the base member slide relative to one another between a first position and a second position, the first position at which the holding element extends distally from the attached deployment tip, and over a length sufficient to receive the mounting of the anchor sleeve on the outer surface thereof, and the second position at which the length of the holding element is recessed proximally from the at least one opening of the attached deployment tip; and the deployment tip is configured to engage an end of the anchor sleeve, when the anchor sleeve is mounted on the holding element, the deployment tip is attached to the base member, and the holding element extends through the at least one opening of the deployment tip, the engagement with the end of the anchor sleeve for pushing the mounted anchor sleeve distally along the outer surface of the holding element as the holding element and base member slide from the first position to the second position.

13. The tool of claim 12, wherein the deployment tip further comprises opposing arms; and the distal segment of the sidewall of the base member includes grooves configured to mate with ends of the opposing arms of the deployment tip, for the attachment of the deployment tip to the distal segment.

14. The tool of claim 12, wherein the holding element comprises at least two tubular members extending side-by-side and approximately parallel with one another, the outer surface of the holding element defining an outer diameter of each tubular member, and the conduit of the holding element comprising a lumen of each of the tubular members.

15. The tool of claim 12, further comprising:
a handle member attached to a proximal end of the holding element, the handle member configured to facilitate sliding the base member and the holding element relative to one another, when the holding element extends through the at least one opening of the attached deployment tip; and
wherein the handle member includes opposing arms and an inner ridge, the proximal end of the holding element being attached to the inner ridge of the handle member; and
the opposing arms engage the base member so that the inner ridge is located within the channel of the base member.

16. The tool of claim 12, further comprising:
a handle member attached to a proximal end of the holding element, the handle member configured to facilitate sliding the base member and the holding element relative to one another, when the holding element extends through the at least one opening of the attached deployment tip; and
wherein the sidewall of the base member further includes a rail segment and a proximal segment, the rail segment extending between the distal segment and shoulders of the proximal segment; and
the handle member includes opposing arms that engage the rail segment of the sidewall of the base member, to hold the handle member and attached holding element in sliding engagement with the base member, along the rail segment, the sliding engagement being stopped by the shoulders of the proximal segment.

17. The tool of claim 12, wherein the outer surface of the holding member comprises a lubricious coating.

18. A tool kit for deploying an anchor sleeve onto at least one implantable medical device, the tool kit comprising:
a plurality of deployment assemblies, at least one of the plurality of deployment assemblies comprising:

a holding element comprising an outer surface and an inner surface, the inner surface defining a conduit of the holding element, the conduit being configured to receive, in sliding engagement, at least one elongate body of the at least one medical device, and the outer surface surrounding the inner surface;
a handle member attached to a proximal end of the holding element, the handle member comprising a gripping feature;
a deployment tip comprising at least one opening through which the holding element extends in sliding engagement, the deployment tip comprising a fitting feature; and
an anchor sleeve mounted on a length of the outer surface of the holding element that extends distal to the at least one opening of the deployment tip; and
a base member comprising a channel and a sidewall, within which the channel extends, the sidewall including a distal segment and a rail segment extending proximally from the distal segment, the distal segment being configured for engagement with the fitting feature of the deployment tip of any one of the at least one of the plurality of deployment assemblies for attachment of the deployment tip thereto, and the rail segment being configured for engagement with the gripping feature of the handle member of any one of the at least one of the plurality of deployment assemblies for attachment of the handle member thereto; and
wherein, when any one of the at least one of the plurality deployment assemblies is attached to the base member, the conduit of the holding element is in communication with the channel, and the channel of the base member receives the corresponding holding element in sliding engagement with the base member and with the attached deployment tip, the attachment of any one of the at least one of the plurality of deployment assemblies to the base member being defined by the attachment of the corresponding deployment tip to the distal segment and the attachment of the corresponding handle member to the rail segment; and
the deployment tip of each deployment assembly is configured to engage with an end of the corresponding anchor sleeve, so that, when any one of the deployment assemblies is attached to the base member, the sliding engagement of the corresponding holding member with the corresponding deployment tip allows the deployment tip to push the corresponding anchor sleeve distally along the holding element.

19. The kit of claim 18, wherein the holding member of one of the at least one of the plurality of deployment assemblies comprises at least two tubular members extending side-by-side and approximately parallel with one another, the outer surface of the holding element defining an outer diameter of each tubular member, and the conduit of the holding element comprising a lumen of each of the tubular members.

20. The kit of claim 18, wherein:
the fitting feature of the deployment tip of the at least one of the plurality of deployment assemblies comprises opposing arms extending proximally from the corresponding at least one opening; and
the distal segment of the sidewall of the base member includes grooves formed therein, the grooves being configured to mate with ends of the opposing arms of each of the deployment tips.

21. The kit of claim 18, wherein the gripping feature of the handle member of the at least one of the plurality of deployment assemblies comprises opposing arms configured to wrap around the rail segment of the base member.

22. A method for deploying an anchor sleeve onto at least one elongate implantable medical device body, the method comprising the steps of:
- selecting and removing one of a plurality of deployment assemblies from a tool kit, each deployment assembly of the tool kit including an anchor sleeve, a holding element, and a deployment tip, each anchor sleeve being mounted on a distal portion of the corresponding holding element, and each deployment tip including at least one opening through which the corresponding holding element extends in sliding engagement;
- inserting a proximal length of the at least one elongate device body into a conduit of the holding element of the selected deployment assembly;
- removing a base member from the tool kit and attaching the selected deployment assembly thereto, so that the at least one opening of the deployment tip is aligned with a channel of the base member, and so that a proximal portion of the holding element is received in the channel for sliding engagement with the base member, the attaching comprising engaging a distal segment of the base member with a fitting feature of the deployment tip of the selected deployment assembly; and
- deploying the anchor sleeve by sliding the holding element relative to the base member and the attached deployment tip, so that the deployment tip engages with an end of the mounted anchor sleeve to move the anchor sleeve distally, off of the holding member and onto the inserted at least one elongate device body.

23. The method of claim 22, wherein engaging the distal segment of the base member with the fitting feature of the deployment tip comprises mating grooves formed in the distal segment with ends of arms of the fitting feature.

24. The method of claim 22, wherein attaching the selected deployment assembly to the base member further comprises engaging a rail segment of the base member with a gripping feature of a handle member of the selected deployment assembly.

25. The method of claim 24, wherein engaging the rail segment of the base member with the gripping feature of the handle member is performed in conjunction with engaging the distal segment of the base member with the fitting feature of the deployment tip.

26. The method of claim 22, wherein inserting the proximal length of the at least one elongate device body follows the attachment of the selected deployment assembly to the base member.

* * * * *